United States Patent

Swidler et al.

[11] 4,098,784
[45] Jul. 4, 1978

[54] RED-1-HYDROXY-3,6-DISULFO-8-ACETAMIDO-2-(3 PHOSPHONOPHENYLAZO)NAPHTHALENE DYES

[75] Inventors: Ronald Swidler; William A. Sanderson, both of Palo Alto, Calif.

[73] Assignee: Burlington Industries, Inc., Greensboro, N.C.

[21] Appl. No.: 710,153

[22] Filed: Jul. 30, 1976

Related U.S. Application Data

[63] Continuation-in-part of Ser. No. 534,349, Dec. 18, 1974, abandoned, which is a continuation-in-part of Ser. No. 441,393, Feb. 11, 1974, abandoned, which is a continuation-in-part of Ser. No. 260,587, Jun. 7, 1972, abandoned.

[51] Int. Cl.² ............... C09B 29/30; D06P 1/06; D06P 3/60
[52] U.S. Cl. .................. 260/199; 260/502.5
[58] Field of Search .......................... 260/199

[56] References Cited

U.S. PATENT DOCUMENTS

| 964,786 | 7/1920 | Kahn et al. ............. 260/199 |
| 2,102,115 | 12/1937 | Fleischhauer et al. ............. 260/199 |
| 2,183,998 | 12/1939 | McNally et al. ............. 260/198 X |
| 2,799,701 | 7/1957 | Whitehouse et al. ............. 260/199 X |
| 2,959,582 | 11/1960 | Schimmelschmidt et al. ....... 260/163 |
| 3,202,550 | 8/1965 | Grossmann et al. ............. 148/6.1 |
| 3,947,435 | 3/1976 | Pechmeze et al. ............. 260/190 |

FOREIGN PATENT DOCUMENTS

| 570,326 | 2/1959 | Belgium ............. 260/197 |
| 1,042,523 | 11/1958 | Fed. Rep. of Germany ....... 260/182 |

*Primary Examiner*—Floyd D. Higel
*Attorney, Agent, or Firm*—Cushman, Darby & Cushman

[57] ABSTRACT

A dye of the formula:

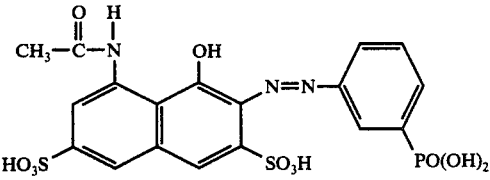

and the alkali metal and ammonium salts thereof are disclosed as novel compositions of matter useful in reactive dyeing of cellulose fibers to give bright red dyeings which exhibit good lightfastness and color strength.

2 Claims, No Drawings

RED-1-HYDROXY-3,6-DISULFO-8-ACETAMIDO-2-(3 PHOSPHONOPHENYLAZO)NAPHTHALENE DYES

CROSS-REFERENCE TO RELATED APPLICATIONS

This application is a continuation-in-part of our copending application, Ser. No. 534,349, filed Dec. 18, 1974 now abandoned, which application Ser. No. 534,349 in turn is a continuation-in-part of application Ser. No. 441,393, filed Feb. 11, 1974, now abandoned, which in turn is a continuation-in-part of application Ser. No. 260,587, filed June 7, 1972, now abandoned.

DESCRIPTION OF THE INVENTION

A class of novel dyes are disclosed herein having the following structural formula:

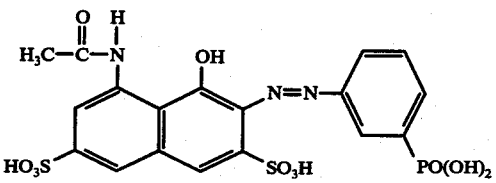

chemically named 1-hydroxy-3,6-disulfo-8-acetamido-2-(3'-phosphonophenylazo)naphthalene. The present invention embraces, in addition to the above-depicted compound, the alkali metal and ammonium salts thereof. These novel bright red azo dyes exhibit properties improved over known materials, i.e., good lightfastness and color strength; they are convenient to use in commercial dyeing operations, reasonably soluble in aqueous solutions (with or without surface active agents, organic solvents or the like) and convenient to synthesize.

We have found, for instance, that the novel dyes herein disclosed are lightfast and are more efficient than other commonly used materials. As an example, where one pound of the novel dye compound is required to dye a given quantity of substrate (such as 100% cotton or another fiber) a greater amount, up to about 1.65 pounds, of another higher molecular weight dye is required to dye the same quantity of material.

The dyes of our invention, while useful as general dyestuff materials, are particularly suitable for reactive dyeing, that is in a process where the dye is reactively linked to cellulose fibers of the substrate to be dyed by means of a phosphorus ester link produced in the presence of a carbodiimide such as cyanamide. This procedure is described in detail in our German Offen. Publication No. 2,505,497 of Aug. 14, 1975, the disclosure of which is hereby incorporated by reference.

Although formulated herein in its free-acid form, the acid dye of the invention may also be made and used in its alkali metal or ammonium salt forms. It preferably is used in free-acid form, more peferably in the ammonium or an acid ammonium salt form. Salts of the dye with amines which are volatile under cure conditions may also be used. The ammonium and acid ammonium salts are conveniently made by adding ammonium hydroxide to solutions of the free-acid dye. Correspondingly, upward adjustments of pH in the dyebath are preferably made with ammonia, less preferably with a volatile amine such as dimethylamine. Downward adjustments of pH, if needed, preferably are made with hydrochloric acid or other acid volatile under curing conditions.

When used at low pH, as exemplified hereinafter, the novel free-acid dye of the invention is used in aqueous solution. At higher pH, the nature of the ammonium or alkali metal salt of the dye in solution will depend upon the ammonia or alkali metal content of the solution as measured by the pH. The ammonium salts are usually the tri- or tetra-ammonium salts, or mixtures thereof, within the general pH range employed. Mixtures of ammonium and alkali metal salts may also be used.

Compounds of our invention are produced by reacting N-acetyl H-acid with diazotized m-aminobenzenephosphonic acid in the presence of suitable adjuncts. The preparation of N-acetyl H-acid is described in Fierz-David, "Fundamental Processes of Dye Chemistry," Interscience Publishers, 1949, at pp. 263–264, the disclosure of which is hereby incorporated by reference. The general reaction of certain naphthol sulfonic acids with 3-aminobenzenephosphonic acid is described in Example 1 of U.S. Pat. No. 3,202,550 to Grossmann et al.

EXAMPLE 1

H acid (Eastman product purified by reprecipitation, 175 g, 0.5 mole), sodium carbonate (30 g), and water (750 ml) were mixed and heated to 50° C to dissolve. Acetic anhydride (85 g, 0.83 mole) was added dropwise over 15 minutes and the solution then stirred for 1 hour at 50° C. Sodium carbonate (75 g) was then added and the solution heated for 1 hour at 95° C to reverse any acylation of the hydroxyl group. The solution was then cooled in ice.

m-Aminophenylphosphonic acid (86.5 g, 0.5 moles) and sodium carbonate (53 g, 0.5 mole) were dissolved in water (500 ml). Sodium nitrite (37 g, 0.54 mole) in water (100 ml) was added, and the solution cooled to 10° C. The solution was added to concentrated hydrochloric acid (125 ml) and ice (500 g). The solution was added all at once to the solution of acetyl H acid, and the solution stirred for 1 hour. Concentrated hydrochloric acid (500 ml) was then added (pH = 0.5) and the solution filtered. The precipitated solid was washed with glacial acetic acid and dried under vacuum at 50° C.

Further purification to the free acid was effected by dissolving the dye in aqueous methanol and passing the solution through an acid ion exchange resin. Removal of the solvent yielded a dye which was, by titration, a tetrabasic acid of greater than 95% purity, thus confirming the structure illustrated above.

As a further means of analysis, the free acid was reacted in solution to make the tri-potassium salt and the solution evaporated to dryness giving the heptahydrated potassium salt having the empirical formula:

$C_{18}H_{13}O_{11}N_3S_2PK_3.7H_2O$

Results of elemental analysis are:

| | |
|---|---|
| Theory: | C 27.5 N 5.4 S 8.1 P 3.9 |
| | H$_2$O 16.0 Molecular Weight 785 |
| Found: | C 26.9 N 5.8 S 7.7 P 3.5 |
| | H$_2$O 15.5 Molecular Weight 789 |

EXAMPLE 2

A printing paste was prepared using 0.05 weight percent of the dye of the formula:

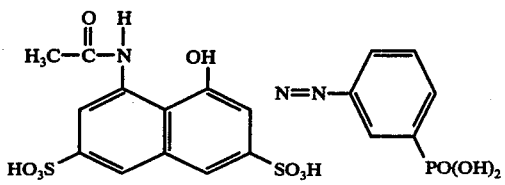

and 0.15 weight percent of a blue dye of the structure:

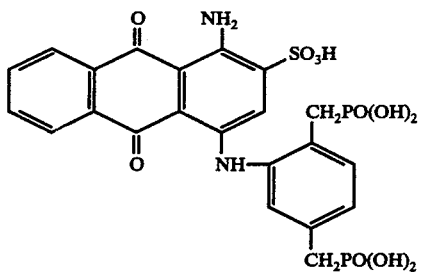

This dye is prepared by reacting bromaminic acid with o-amino-p-xylylenediphosphonic acid as described in Example 25 of our German Offen. P 25 05 497.1.

The print paste also included 0.2 weight percent of a wetting agent (Igepal CO-710, nonylphenoxypoly-(ethyleneoxy)-ethanol having 10-11 ethyleneoxy units, sold by GAF), 0.1 weight percent $(NH_4)_2HPO_4$, 3.0 weight percent of dicyandiamide, 1.0 weight percent of sodium alginate, 33.0 weight percent of 70% Varsol emulsion and the remainder water. The resulting print paste was adjusted to a pH of 8.6 with ammonium hydroxide.

The print paste so prepared was screen printed on 100% cotton fabric at an add-on of about 5 grams per square yard (about a 100% average add-on). The fabric was dried and fixed at 400° F, at an exposure time of 60 seconds, to produce a printed cotton fabric having a good color fixation. This example corresponds in substance to Example 64 of parent application Ser. No. 534,349.

In the following Examples 3–5, all percentages are expressed on the weight of the bath.

EXAMPLE 3

A dye bath containing the following ingredients was prepared:

| | |
|---|---|
| 1.0% | Red dye of Example 1 |
| 3.0% | $H_3PO_4$ (85%) |
| 8.0% | Cyanamide AC-50 (50%) |
| 2.0% | Carbowax 350 |
| 0.25% | Igepal CO-710 |
| pH | 1.5 |

The above bath was padded on 100% cotton at 70% pick-up, dried at 220° F, and cured for 60 seconds at 390° F. The cloth was rinsed; practically no color was removed.

EXAMPLE 4

A bath containing the following ingredients was prepared:

| | |
|---|---|
| 0.5% | Red dye of Example 1 |

-continued

| | |
|---|---|
| 5.0% | Cyanamide AC-50 (50%) |
| 0.5% | Igepal CO-710 |
| 0.3% | $H_3PO_4$ (85%) |
| pH | Adjusted to 5 with $NH_4OH$ |

This bath was padded on 100% cotton, steamed for 1 minute at 220° F and then cured 45 seconds at 390° F. When the cloth was scoured with 1.7 g/l soda ash and 1.5 g/l Synthrapol SP at the boil for 2 minutes, a fixation of 80% was obtained. Fixation is defined herein as that percentage of the color retained on the cloth after scouring, based on the color as it comes from the curing oven, both color measurements being taken on a Beckman DBG Spectrophotometer.

EXAMPLE 5

The following bath was prepared:

| | |
|---|---|
| 2.0% | Red dye of Example 1 |
| 4.0% | Dicyandiamide |
| 0.1% | Igepal CO-710 |
| 0.125% | $H_3PO_4$ (85%) |
| pH | 5 |

This bath was padded on a 50/50 blend of polyester (T54)/cotton at 60% pick-up, infrared pre-dried and cured 75 seconds at 400° F. After scouring as in Example 4, color fixation was 70%.

As noted above, the novel dyes of the invention are unusually efficient, by which it is meant that the color yield per unit of dye weight is exceptional for a dye which is washfast on cellulosic fabrics and yarns. The exceptional efficiency stems from the fact that the dyes give inherently intense bright red dyeings, coupled with the fact that their molecular weights are very low by comparison with the large-molecule direct dyes which are substantive to cellulosics. Hence each molecule, which is to say, each low molecular weight of it, provides a high yield of color on a pound-for-pound basis.

The low molecular weight, or expressed otherwise, the general simplicity and smallness of the molecule, provide yet another advantage to the dyes of the invention. Especially when a dye is permanently fixed to a substrate by chemical reaction, it is highly desirable that any of the dye which has failed to become reactively bound should be readily washed away during process rinsing, to provide easy washoff, and reduce subsequent "washdown" during use. In the dyes of the invention, the same phosphonic acid group which provides a site for reaction also serves as a strong water-solubilizing group for aiding removal of any dye molecules which are not fixed, thereby insuring efficient removal of unfixed dye during process rinsing, and reducing or even eliminating subsequent drawn-out washdown during customer use. The red dyes of the invention are believed to be easier to wash off in process rinsing than any red dye being used in commercial continuous dyeing today.

The acetyl group is provided in the dyes as the smallest group capable of overcoming the inherent susceptibility to light of H-acid dyes. Other groups will furnish lightfastness properties, but no other so efficiently as the acetyl. In other words, the acetyl group supplies lightfastness in conjunction with minimum effect on the high redness per pound of the dyes of the invention.

The dyes of the invention have a distinct advantage, compared to conventional reactive dyes which are applied under strongly alkaline conditions, that they mostly are applied under acidic conditions and thus may be applied together with disperse dyes in the same dyebath. Alkaline conditions lead to flocculation of the majority of disperse dyes, which fact drastically limits the possibilities for simultaneous dyeings of polyester and cotton with disperse and conventional reactive dyes. In contrast, the acid fixing conditions used with the phosphonic dyes of the invention have no adverse effect on disperse dyes, and the two types of dyes can be used together without difficulty.

What is claimed is:

1. A dye of the formula:

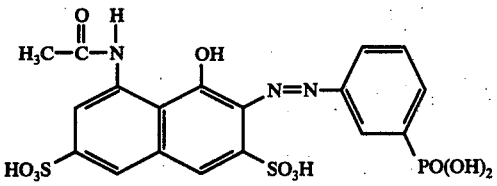

or the ammonium or an alkali metal salt thereof.

2. The ammonium salt of the dyestuff of claim 1.